United States Patent
Barker et al.

(10) Patent No.: US 10,052,083 B2
(45) Date of Patent: Aug. 21, 2018

(54) ACTUATOR FOR MOVING AN ULTRASOUND PROBE

(71) Applicant: UNIVERSITY OF WESTERN ONTARIO, London (CA)

(72) Inventors: Kevin Barker, London (CA); Aaron Fenster, London (CA); Hamid Neshat, London (CA); Nirmal Kakani, London (CA)

(73) Assignee: UNIVERSITY OF WESTERN ONTARIO (CA)

( * ) Notice: Subject to any disclaimer, the term of this patent is extended or adjusted under 35 U.S.C. 154(b) by 223 days.

(21) Appl. No.: 14/388,967

(22) PCT Filed: Mar. 28, 2013

(86) PCT No.: PCT/CA2013/000302
§ 371 (c)(1),
(2) Date: Sep. 29, 2014

(87) PCT Pub. No.: WO2013/142978
PCT Pub. Date: Oct. 3, 2013

(65) Prior Publication Data
US 2015/0018685 A1    Jan. 15, 2015

Related U.S. Application Data

(60) Provisional application No. 61/617,031, filed on Mar. 28, 2012.

(51) Int. Cl.
*A61B 8/00* (2006.01)
*A61B 8/13* (2006.01)
(Continued)

(52) U.S. Cl.
CPC .............. *A61B 8/4461* (2013.01); *A61B 8/13* (2013.01); *A61B 8/4218* (2013.01); *A61B 8/483* (2013.01);
(Continued)

(58) Field of Classification Search
CPC ....... A61B 8/13; A61B 8/4218; A61B 8/4461; A61B 8/466; A61B 8/483; A61B 8/5207;
(Continued)

(56) References Cited

U.S. PATENT DOCUMENTS

| 4,290,309 A | 9/1981 | Charlebois et al. |
| 5,445,154 A | 8/1995 | Larson et al. |

(Continued)

FOREIGN PATENT DOCUMENTS

| CA | 2749465 A1 | 2/2012 |
| CN | 102497131 A | 6/2012 |

(Continued)

OTHER PUBLICATIONS

Supplementary European Search Report to corresponding European Appl. No. 13 76 7924, dated Oct. 9, 2015, 9 pages.

*Primary Examiner* — Michael Rozanski
(74) *Attorney, Agent, or Firm* — Tarolli, Sundheim, Covell & Tummino LLP

(57) ABSTRACT

An actuator for an ultrasound probe comprises a housing assembly configured to accommodate an ultrasound probe and to be positioned adjacent to a target region of interest to be examined, and a motor assembly coupled to the housing assembly, the motor assembly configured to move the housing assembly in a manner to allow an ultrasound probe when accommodated by the housing assembly to perform a compound scan of the target region of interest.

20 Claims, 12 Drawing Sheets

(51) Int. Cl.
*A61B 8/08* (2006.01)
*G01N 29/22* (2006.01)
*G01N 29/265* (2006.01)

(52) U.S. Cl.
CPC .............. *A61B 8/5253* (2013.01); *A61B 8/54* (2013.01); *G01N 29/225* (2013.01); *G01N 29/265* (2013.01); *A61B 8/466* (2013.01); *A61B 8/5207* (2013.01)

(58) Field of Classification Search
CPC ...... A61B 8/5253; A61B 8/54; G01N 29/225; G01N 29/265
See application file for complete search history.

(56) References Cited

U.S. PATENT DOCUMENTS

| | | |
|---|---|---|
| 5,456,256 A | 10/1995 | Schneider et al. |
| 5,487,388 A | 1/1996 | Rello et al. |
| 5,562,095 A | 10/1996 | Downey et al. |
| 6,524,246 B1 * | 2/2003 | Kelly .................. A61B 8/0825 600/437 |
| 2009/0326554 A1 | 12/2009 | Vohra et al. |
| 2010/0030078 A1 | 2/2010 | Mikami |
| 2011/0152690 A1 | 6/2011 | Anthony et al. |
| 2011/0224551 A1 | 9/2011 | Barnard et al. |

FOREIGN PATENT DOCUMENTS

| | | |
|---|---|---|
| GB | 2027197 | 2/1980 |
| WO | 9600402 | 1/1996 |
| WO | 0230287 | 4/2002 |

* cited by examiner

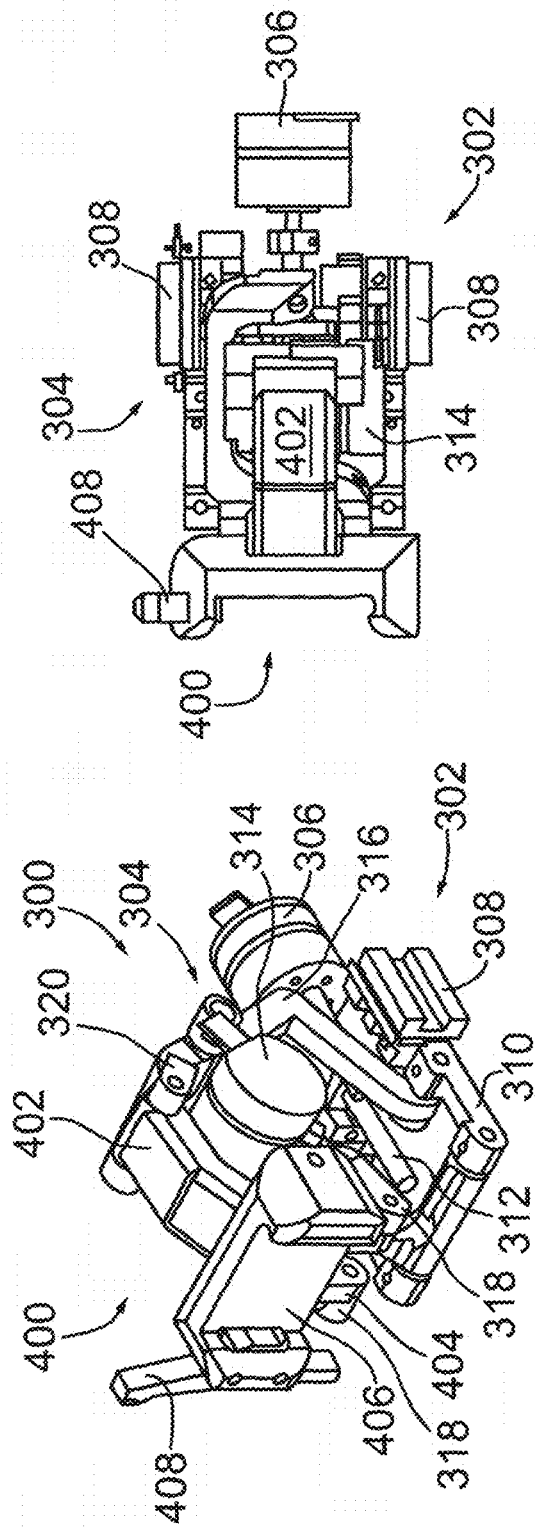

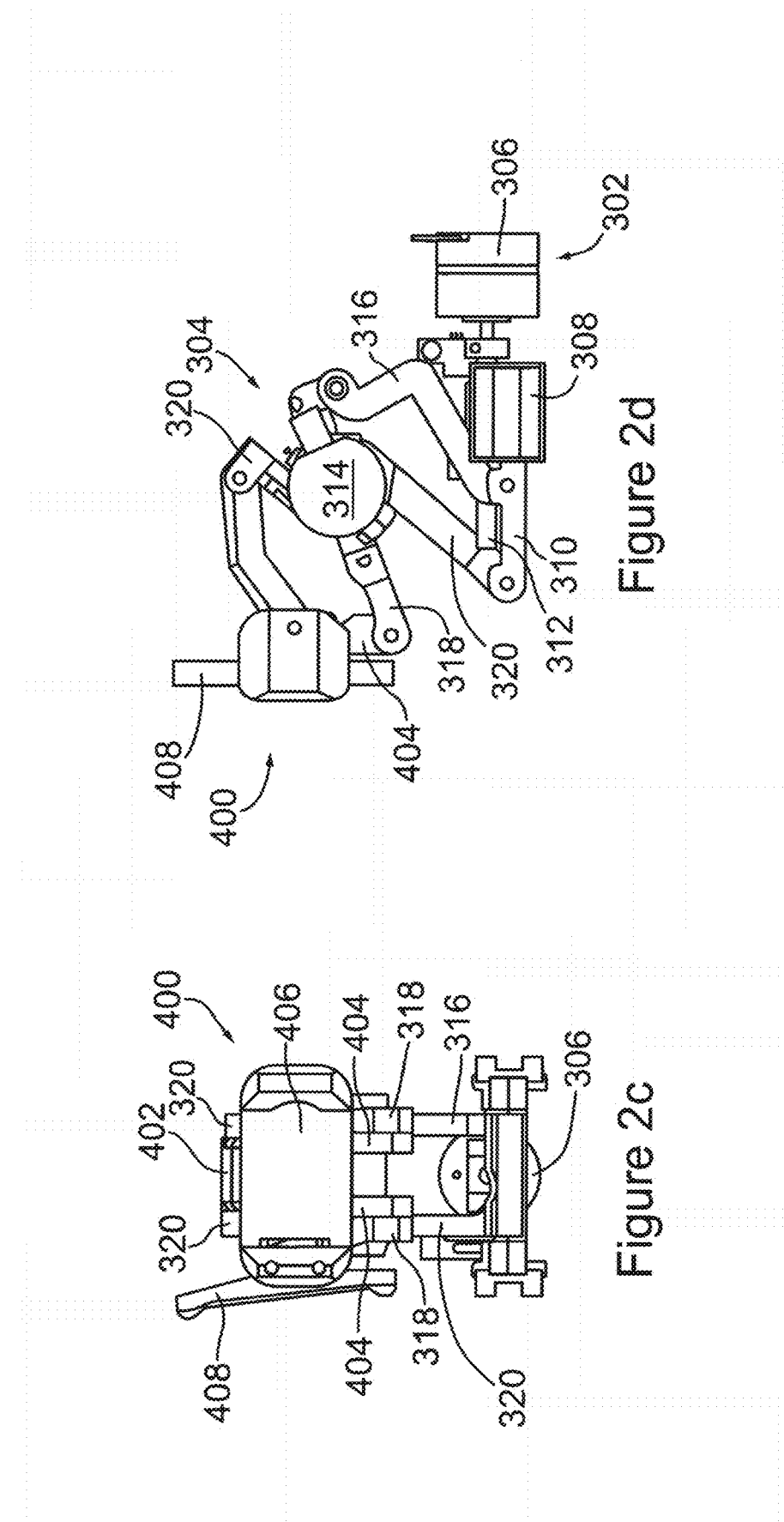

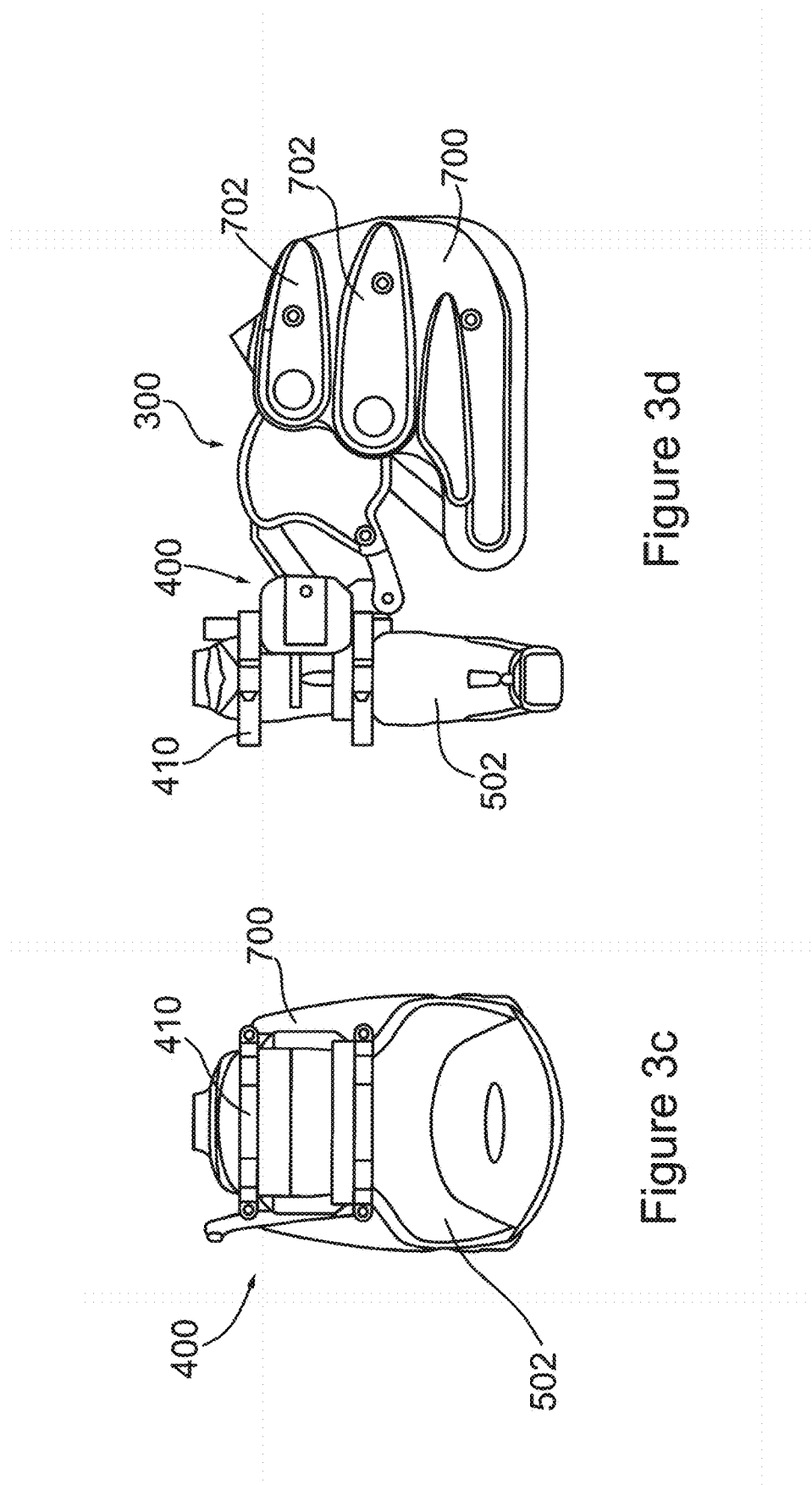

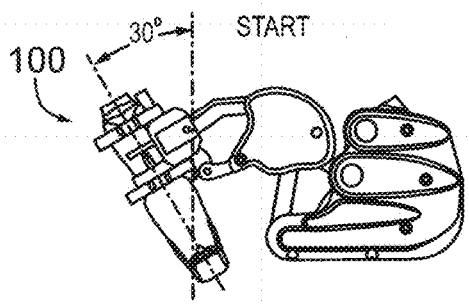
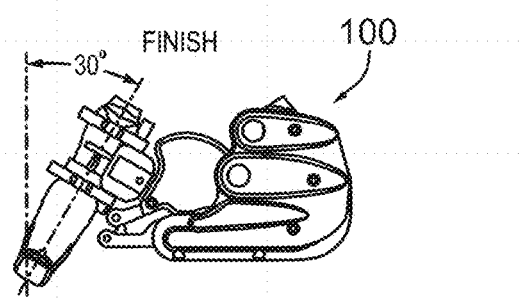
Figure 7a  Figure 7b
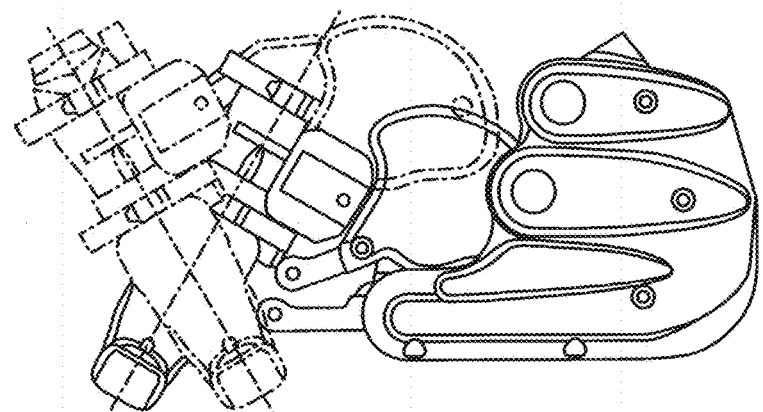
Figure 7c

ACTUATOR FOR MOVING AN ULTRASOUND PROBE

CROSS-REFERENCE TO RELATED APPLICATION

This application is a national stage application from International Application No. PCT/CA2013/000302, filed Mar. 28, 2013, and entitled "ACTUATOR FOR MOVING AN ULTRASOUND PROBE", which in turn claims the benefit of U.S. Provisional Application No. 61/617,031 to Barker et al. filed on Mar. 28, 2012, the entire disclosure of each of which is incorporated herein by reference.

FIELD OF THE INVENTION

The present invention relates to ultrasound imaging and in particular, to an actuator for moving an ultrasound probe and to an ultrasound imaging system employing the same.

BACKGROUND OF THE INVENTION

A wide variety of approaches have been developed to produce three-dimensional (3D) ultrasound images using both one-dimensional (1D) ultrasound arrays and two-dimensional (2D) ultrasound arrays. The use of 1D ultrasound arrays to produce 3D ultrasound images requires methods to determine the position and orientation of acquired 2D ultrasound images within the 3D ultrasound image volume. The use of 2D ultrasound arrays to produce 3D ultrasound images requires a 3D scan-converter to build the 3D ultrasound images from the sequence of transmit acoustic signals.

U.S. Pat. No. 5,562,095 to Downey et al., the entire disclosure of which is incorporated herein by reference, discloses a 3D ultrasound imaging system for the eye, prostate and other organs, comprising an assembly onto which an ultrasound probe may be mounted, a motor and drive for either rotating or scanning the ultrasound probe relative to the human organ under investigation, and a computer for executing software for controlling movement of the assembly to rotate or scan the ultrasound probe. Ultrasound signals from the probe are processed via a clinical ultrasound machine for generating multiple 2D ultrasound images of the organ. The software executed on the computer collects the 2D ultrasound images of the clinical ultrasound machine and reconstructs the 2D ultrasound images to form a 3D ultrasound image which can be viewed and manipulated in real time, or stored for later retrieval.

Improvements in 3D ultrasound imaging are generally desired. It is therefore an object at least to provide a novel actuator for moving an ultrasound probe and a novel ultrasound imaging system employing the same.

SUMMARY OF THE INVENTION

Accordingly, in one aspect there is provided an actuator for an ultrasound probe comprising a housing assembly configured to accommodate an ultrasound probe and to be positioned adjacent a target region of interest to be examined, and a motor assembly coupled to the housing assembly, the motor assembly configured to move the housing assembly in a manner to allow an ultrasound probe when accommodated by the housing assembly to perform a compound scan of the target region of interest.

In one embodiment, during the compound scan, the motor assembly is configured to move the housing assembly along a linear path and to tilt the housing assembly during its movement along the linear path. The motor assembly comprises a first motor system and a second motor system, the first motor system being configured to move the housing assembly along the linear path and the second motor system being configured to tilt the housing assembly. The first motor system comprises a motor coupled to a linear slide for moving the housing assembly along the linear path. The second motor system comprises a motor coupled to a plurality of linkage arms for tilting the housing assembly between first and second boundaries.

In one embodiment, the motor assembly is further configured to move the housing assembly along the linear path to allow the ultrasound probe when accommodated by the housing assembly to perform a linear scan of the target region of interest or to tilt the housing assembly to allow the ultrasound probe when accommodated by the housing assembly to perform a tilt scan of the target region.

In one embodiment, the housing assembly comprises a harness to retain the ultrasound probe therein. A casing encloses at least the motor assembly and has user actuatable controls thereon. Formations are provided in the casing to accommodate a user's fingers and the user actuatable controls are positioned approximate the formations.

According to another aspect there is provided an ultrasound imaging system comprising the above actuator, an ultrasound probe accommodated by the housing assembly of the actuator, and processing structure configured to process ultrasound signals output by the ultrasound probe and to control the motor assembly of the actuator.

According to another aspect there is provided a method of reconstructing a three-dimensional ultrasound image of a target region of interest, the method comprising: receiving a plurality of 2D ultrasound images captured during a compound scan of the target region of interest; and mapping pixels of each of the received 2D ultrasound images to a corresponding voxel within a reconstruction matrix.

In one embodiment, the 2D ultrasound images are received in succession. Each pixel of each 2D ultrasound image is mapped to a corresponding voxel within the reconstruction matrix. The reconstruction matrix is displayed on a display device. A mapping matrix is calculated to map pixels of each received 2D ultrasound image to the corresponding voxel within the reconstruction matrix.

According to yet another aspect there is provided a method of reconstructing a three-dimensional ultrasound image of a target region of interest, the method comprising: calculating a mapping matrix to map pixels within an acquisition matrix to a corresponding voxel within a reconstruction matrix; receiving a plurality of 2D ultrasound images captured during a compound scan of the target region of interest and storing pixels of each of the plurality of 2D ultrasound images within the acquisition matrix; mapping each pixel within the acquisition matrix with a corresponding voxel within the reconstruction matrix using the mapping matrix; and storing a pixel value associated with each pixel within the acquisition matrix at the corresponding voxel within the reconstruction matrix.

BRIEF DESCRIPTION OF THE DRAWINGS

Embodiments will now be described more fully with reference to the accompanying drawings in which:

FIG. 2a is an isometric view of a motor assembly and a housing assembly forming part of an actuator of the 3D ultrasound imaging system of FIG. 1;

FIG. 2b is a top plan view of the motor assembly and the housing assembly of FIG. 2a;

FIG. 2c is a front elevational view of the motor assembly and the housing assembly of FIG. 2a;

FIG. 2d is a side elevational view of the motor assembly and the housing assembly of FIG. 2a;

FIG. 3c is a front elevational view of the motor assembly, the housing assembly, the ultrasound probe and the casing;

FIG. 3d is a side elevational view of the motor assembly, the housing assembly, the ultrasound probe and the casing;

FIGS. 7a to 7c are side elevational views of the 3D ultrasound imaging system of FIG. 1 during operation in a compound scanning mode;

DETAILED DESCRIPTION OF THE EMBODIMENTS

In the following, an actuator for an ultrasound probe and an ultrasound imaging system employing the same are described. The actuator comprises a housing assembly configured to accommodate an ultrasound probe and to be positioned adjacent to a target region of interest to be examined. The region of interest may be a human organ or tissue such as for example a liver, a kidney, a breast, etc. A motor assembly is coupled to the housing assembly and is configured to move the housing assembly and hence the ultrasound probe, in a manner to allow the ultrasound probe when accommodated by the housing assembly to perform a compound scan of the target region of interest.

Figure 1:
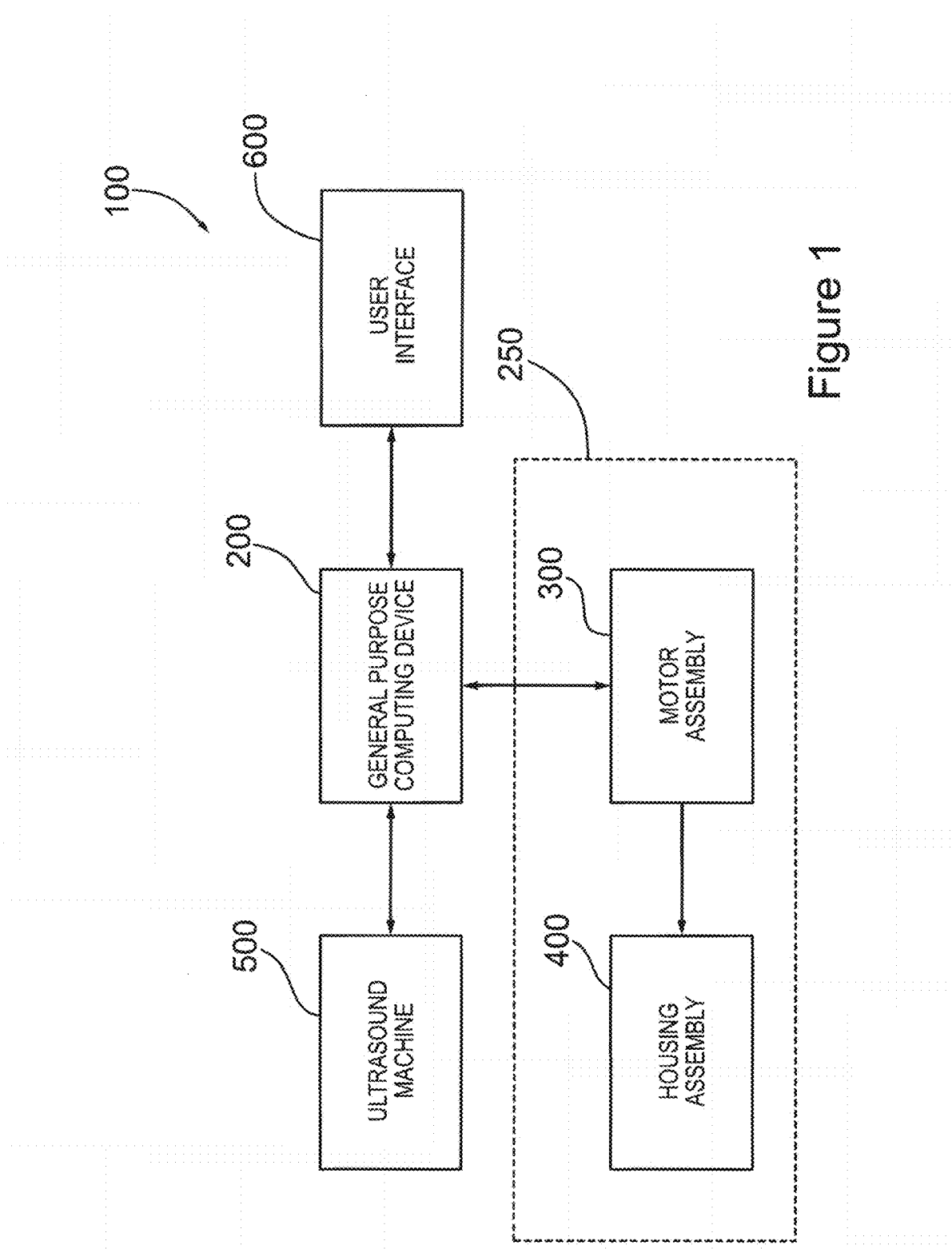
FIG. 1 is a schematic block diagram of a 3D ultrasound imaging system.
Figure 2E:
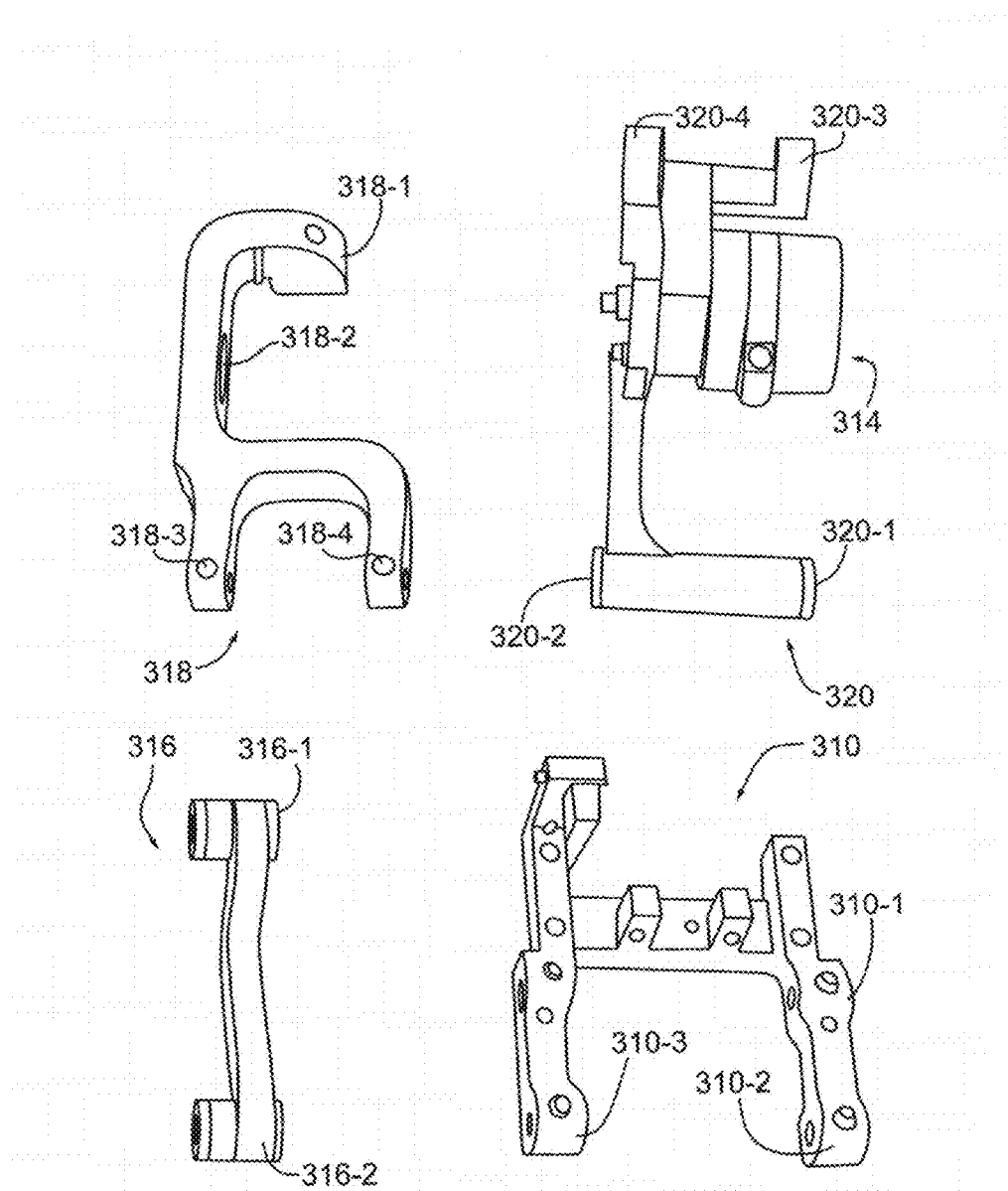
FIG. 2e is a top plan view of the motor assembly disassembled.

Turning now to FIG. 1, a schematic block diagram of a 3D ultrasound imaging system 100 is shown. In this embodiment, the 3D ultrasound imaging system 100 is operable in a plurality of modes including a linear scanning mode, a tilt scanning mode, and a compound scanning mode, as will be described. The 3D ultrasound imaging system 100 comprises a general purpose computing device 200 that is communicatively coupled to an actuator 250. The actuator 250 comprises a motor assembly 300 and a housing assembly 400. The motor assembly 300 receives control commands from the general purpose computing device 200 and in response, moves the housing assembly 400. The housing assembly 400 accommodates an ultrasound probe 502 (see FIGS. 3a to 3d) that communicates with a clinical ultrasound machine 500. The clinical ultrasound machine 500 processes ultrasound signals received from the ultrasound probe 502 during scanning of a target region of interest to generate 2D ultrasound images of the region of interest. The clinical ultrasound machine 500 is communicatively coupled to the general purpose computing device 200 and sends generated 2D ultrasound images thereto. The general purpose computing device 200 in turn processes the received 2D ultrasound images to reconstruct a 3D ultrasound image of the target region of interest, which is communicated to a user interface 600 for display thereon.

The general purpose computing device 200 in this embodiment is a personal computer or other suitable processing device comprising, for example, a processing unit, system memory (volatile and/or non-volatile memory), other non-removable or removable memory (e.g., a hard disk drive, RAM, ROM, EEPROM, CD-ROM, DVD, flash memory, etc.) and a system bus coupling the various computing device components to the processing unit. The general purpose computing device 200 may also comprise networking capability using Ethernet, WiFi, and/or other network format, to access shared or remote drives, one or more networked computers, or other networked devices.

Figures 3A, 3B:
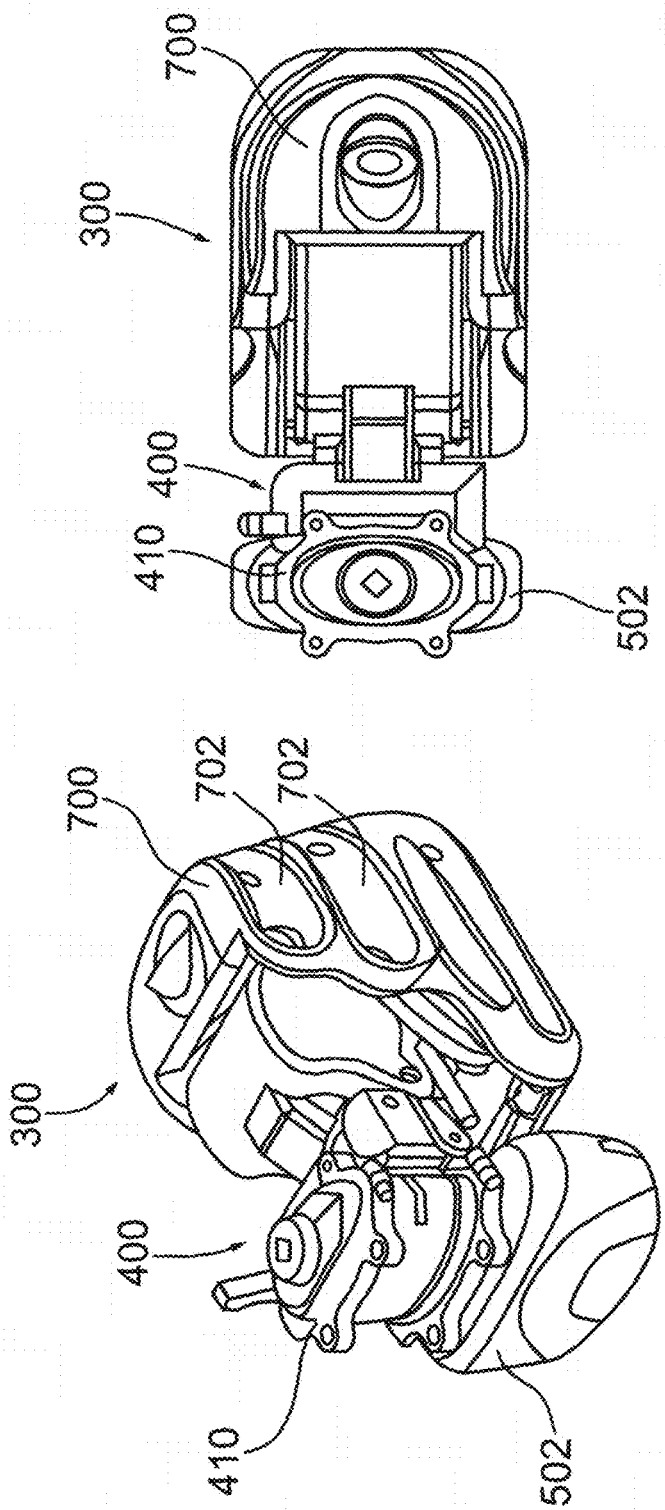
FIG. 3a is an isometric view of the motor assembly, the housing assembly, an ultrasound probe and a casing.
FIG. 3b is a top plan view of the motor assembly, the housing assembly, the ultrasound probe and the casing.

FIGS. 2a to 2e illustrate the motor assembly 300 and the housing assembly 400 and FIGS. 3a and 3d illustrate the motor assembly 300, the housing assembly 400, the ultrasound probe 502, and a casing 700 enclosing the motor assembly 300 and a portion of the housing assembly 400.

In this embodiment, motor assembly 300 comprises a linear motor system 302 and a tilt motor system 304. The linear motor system 302 comprises a motor 306 coupled to a linear slide carriage 310 via a lead screw 312. Each side of the linear carriage 310 is connected to a linear slide 308. Each linear slide 308 is slidably mounted to a respective stationary rail which is connected to an interior surface of the casing 700, as will be described. As the motor 306 rotates the lead screw 312, the linear slide carriage 310 moves along a linear path. The movement of the linear slide carriage 310 causes movement of each linear slide 308 along its respective stationary rail. As such, the linear motor system 302 moves the housing assembly 400 along the linear path. In this embodiment, the motor 306 has a gear ratio of about 112:1 and a maximum no load output speed of about 59 revolutions-per-minute (RPM). The lead screw 312 has a pitch of about 1/2.7 inches. The linear motor system 302 is configured to move the linear slides 308 a total of about 3 cm along the linear path at a speed of about 0.75 cm/s.

The tilt motor system 304 comprises a motor 314 and a plurality of linkage arms 316, 318 and 320 formed of aluminum or other suitable material. The tilt motor system 304 is shown disassembled in FIG. 2e together with linear slide carriage 310. The linkage arms 316, 318 and 320 and linear slide carriage 310 are connected to one another, as will be described, via a polyether ether ketone (PEEK) bushing on a stainless steel shaft. A first connection point 316-1 of linkage arm 316 is connected to a first connection point 318-1 of linkage arm 318. A second connection point 316-2 of linkage arm 316 is connected to the linear slide carriage 310 at connection point 310-1. A front end defined by connection points 320-1 and 320-2 of linkage arm 320 is connected to the linear slide carriage 310 at connection points 310-2 and 310-3, respectively. A back end of linkage arm 320 defined by connection points 320-3 and 320-4 is connected to housing assembly 400. A connection point 318-2 of linkage arm 318 is connected to a driving shaft (not shown) of motor 314. Linkage arm 318 is connected to a lower portion of housing assembly 400 at connection points 318-3 and 318-4. As will be appreciated, motor 314, when actuated, imparts rotation of linkage arm 318. As a result of the rotation, linkage arms 316 and 320 rotate and thus, the tilt motor system 304 provides tilt motion to housing assembly 400 between a range of about −30° and 30°. In this embodiment, the motor 314 has a gear ratio of about 207:1 and a maximum no load output speed of about 32 RPM. The tilt motor system 304 is configured to complete a 60° sweep in about 4 seconds.

Housing assembly 400 comprises a linkage arm 402 connected to the connection points 320-3 and 320-4 of linkage arm 320. A bottom portion 404 of the housing assembly 400 is connected to connection points 318-3 and 318-4 of linkage arm 318. The housing assembly 400 has a housing port 406 dimensioned to securely hold a harness 410 that is configured to retain the ultrasound probe 502. A handle 408 is tangentially connected to a side of the housing assembly 400. The top of the handle 408 comprises a locking button for locking the harness 410 therein. The bottom of the handle 408 comprises an unlocking button for unlocking the harness 410 therefrom. In this embodiment, the housing assembly 400, including the linkage arm 402 and handle 408, is made of a polyether ether ketone (PEEK) material. Harness 410 is positioned around a top portion of the ultrasound probe 502 and retains the ultrasound probe 502. The harness 410 is custom made for different types of ultrasound probes. The harness 410 is opened by loosening a screw associated therewith and when opened, the harness 410 is able to receive the ultrasound probe 502.

The casing 700 in this embodiment is made of a molded plastic material such as for example ABS-M30 manufactured by Stratasys®. The interior surface of the casing 700 comprises a pair of stationary rails (not shown). Each stationary rail extends along a respective side of the interior surface of the casing 700 and is configured to support a respective linear slide 308. Each side of the exterior surface of the casing 700 has a pair of grooves 702 formed therein, each of which is dimensioned to receive a finger of a user. A plurality of operational buttons is positioned within the grooves 702. The buttons can be user actuated to allow the user to control and operate the 3D ultrasound imaging system 100. Exemplary functions associated with the operational buttons include start scan, stop scan, jog, etc.

The user interface 600 in this embodiment comprises a display monitor such as for example a liquid crystal display (LCD) panel or other suitable display panel or device connected to the general purpose computing device 200 via a cable such as for example a high-definition multimedia interface (HDMI) cable or a video graphics array (VGA) cable or other suitable wired or wireless communications link. The user interface 600 displays the graphical user interface of an application program executed by the general purpose computing device 200. The user interface 600 further comprises a keyboard and a mouse and/or other suitable user input devices, which are connected to the general purpose computing device 200 via a universal serial bus (USB) cable or other suitable wired or wireless connection.

Figure 4:
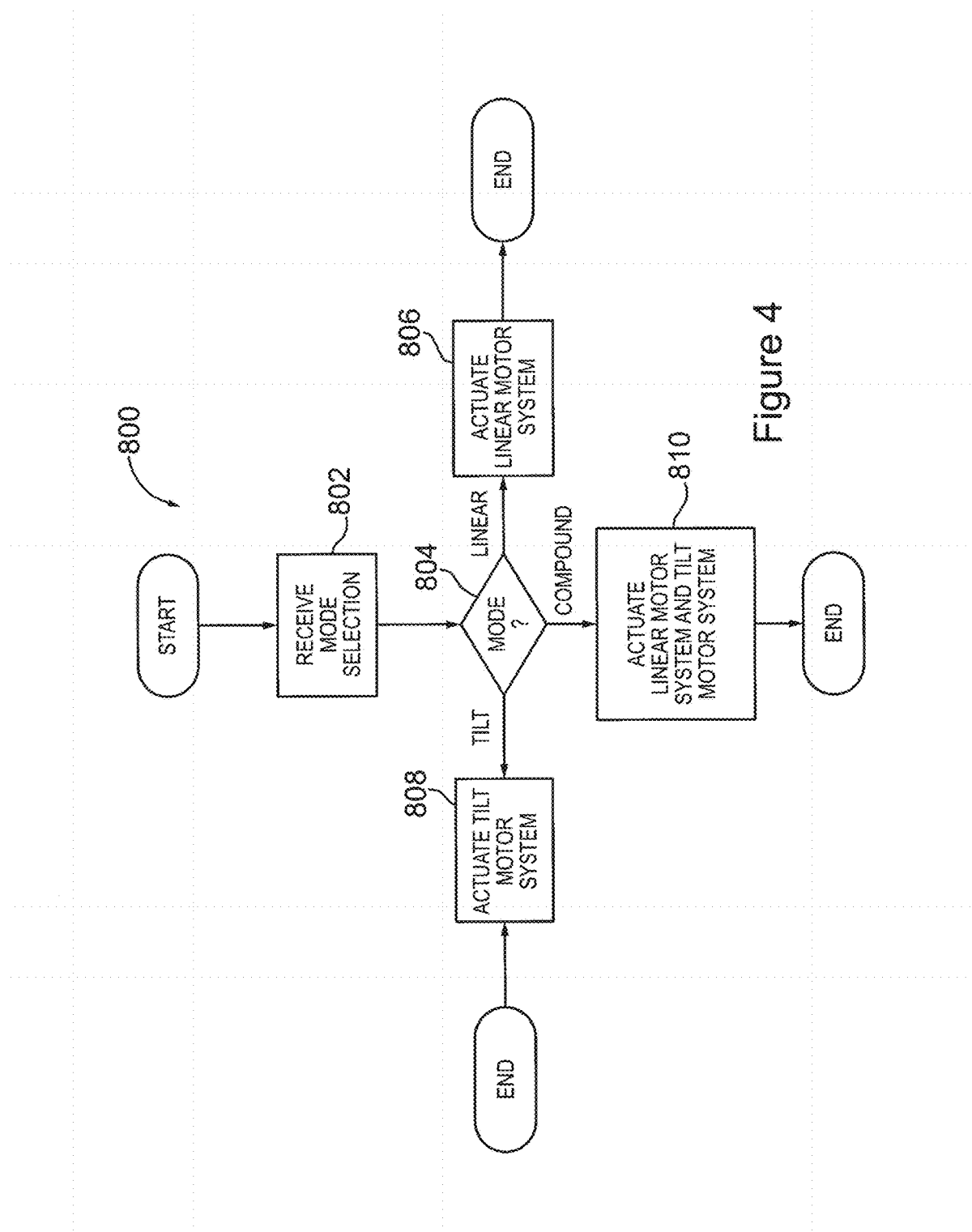
FIG. 4 is a flowchart showing a 3D ultrasound imaging system operation method.

Turning now to FIG. 4, a method of operating the 3D ultrasound imaging system 100 is shown and is generally identified by reference numeral 800. During operation, when the general purpose computing device 200 receives a mode selection from the user interface 600 (step 802), a check is performed to determine which mode has been selected (step 804). If the linear scanning mode has been selected, when a start scan command has been input via actuation of the associated operational button, the linear motor system 302 is actuated by the general purpose computing device 200 (step 806) and thus, a linear scan of the target region of interest is performed by the 3D ultrasound imaging system 100, and the method ends. If the tilt scanning mode has been selected, when a start scan command has been input via actuation of the associated operational button, the tilt motor system 304 is actuated by the general purpose computing device 200 (step 808) and thus, a tilt scan of the target region of interest is performed by the 3D ultrasound imaging system 100, and the method ends. If the compound scanning mode has been selected, when a start scan command has been input via actuation of the associated operational button, both the linear motor system 302 and the tilt motor system 304 are actuated by the general purpose computing device 200 (step 810) and thus a compound scan of the target region of interest is performed by the 3D ultrasound imaging system 100, and the method ends.

Figure 5A:
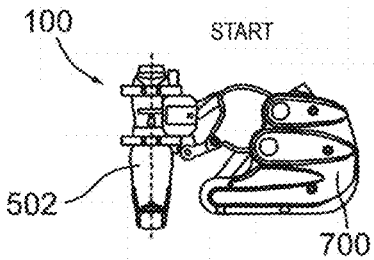
FIGS. 5a to 5c are side elevational views of the 3D ultrasound imaging system of FIG. 1 during operation in a linear scanning mode.

Turning to FIG. 5a, the start position of the actuator 250 in the linear scanning mode is shown. As can be seen, ultrasound probe 502 is positioned such that its longitudinal axis is generally normal to the surface of the target region of interest to be scanned. Each linear slide 308 is at its rearward most position on the respective stationary rail. As will be appreciated, each linear slide 308 is contained within casing 700, and thus is not visible in FIG. 5a.

Figure 5B:
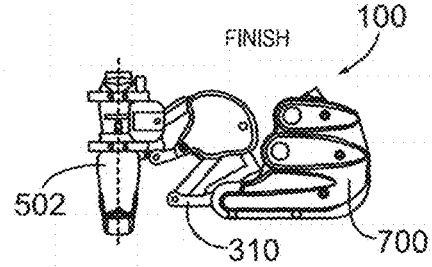

FIG. 5b shows the finish position of the actuator 250 in the linear scanning mode. As can be seen, ultrasound probe 502 remains positioned such that its longitudinal axis is generally normal to the surface of the target region of interest to be scanned. Each linear slide 308 is at its forward most position on the respective stationary rail. As such, the linear slide carriage 310 extends out of casing 700. Again, as each linear slide 308 is contained within casing 700, it is not visible in FIG. 5b.

Figure 5C:
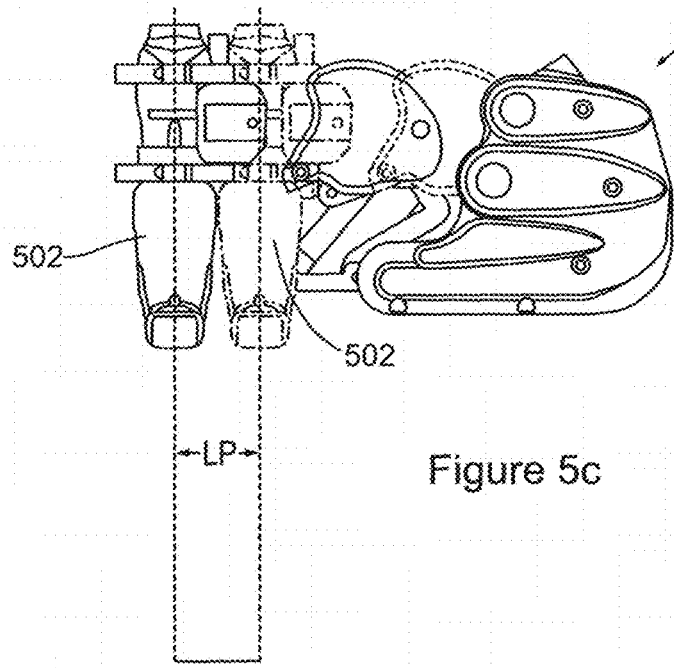

FIG. 5c shows both the start position and the finish position of the actuator 250 in the linear scanning mode. As can be seen, the ultrasound probe 502 moves from the start position to the finish position along a linear path indicated by arrow LP. The linear path LP is defined by movement of the linear slide carriage 310 and the resultant movement of each linear slide 308 along its respective stationary rail. As such, the ultrasound probe 502 performs a linear scan of the target region of interest when moved along linear path LP. It will be appreciated that in the linear scanning mode, there is no tilt movement of the ultrasound probe 502.

During operation in the linear scanning mode, the ultrasound probe 502 scans the target region of interest as it moves along the linear path LP and outputs ultrasound signals to the clinical ultrasound machine 500. The ultrasound signals from the ultrasound probe 502 are processed via the clinical ultrasound machine 500 to generate a plurality of 2D ultrasound images of the target region of interest at the desired frame rate (typically 15 or 30 frames per second). The 2D ultrasound images are then communicated to the general purpose computing device 200 for processing. The general purpose computing device 200 processes the 2D ultrasound images to reconstruct a 3D ultrasound image covering a rectangular volume of the scanned target region of interest according to a known method such as that described in above-incorporated U.S. Pat. No. 5,562,095 to Downey et al.

Figure 6A:
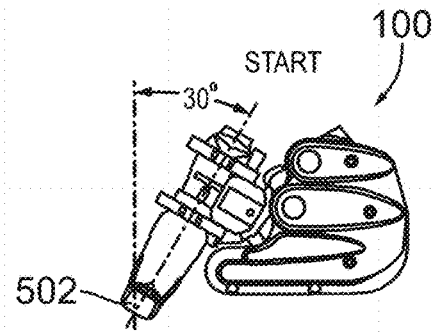
FIGS. 6a to 6c are side elevational views of the 3D ultrasound imaging system of FIG. 1 during operation in a tilt scanning mode.

Turning to FIG. 6a, the start position of the actuator 250 in the tilt scanning mode is shown. As can be seen, ultrasound probe 502 is positioned such that its longitudinal axis is approximately 30° to the normal of the surface of the target region of interest to be scanned. Each linear slide 308 is at its rearward most position on the respective stationary rail. As will be appreciated, each linear slide 308 is contained within casing 700, and thus is not visible in FIG. 6a.

Figure 6B:
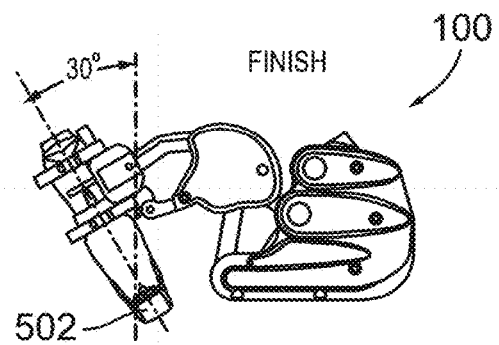

FIG. 6b shows the finish position of the actuator 250 in the tilt scanning mode. As can be seen, ultrasound probe 502 is positioned such that its longitudinal axis is approximately −30° to the normal of the surface of the target region of interest to be scanned. Each linear slide 308 is at its rearward most position on the respective stationary rail. As will be appreciated, each linear slide 308 is contained within casing 700, and thus is not visible in FIG. 6b.

Figure 6C:
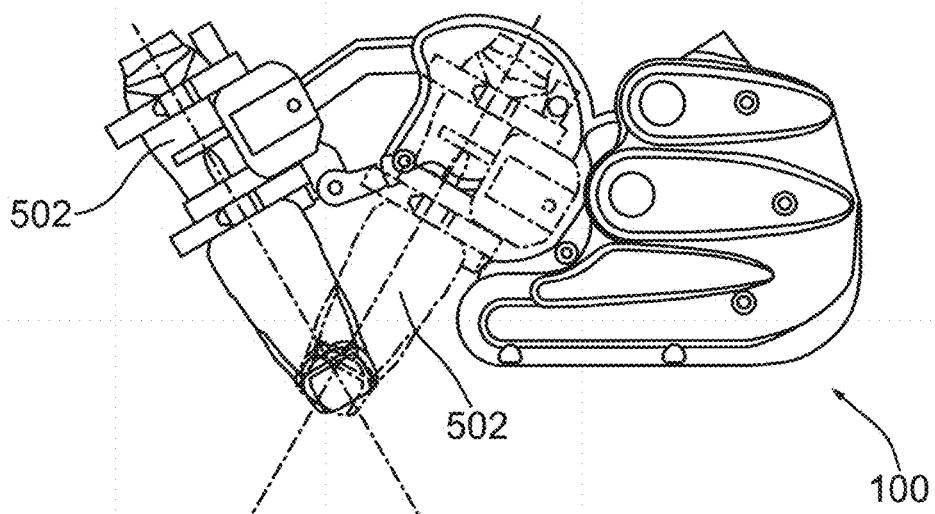

FIG. 6c shows both the start position and the finish position of the actuator 250 in the tilt scanning mode. As can be seen, the ultrasound probe 502 moves from the start position to the finish position along a path indicated by arrow TP. As such, the ultrasound probe 502 performs a tilt scan of the target region of interest when moved along path TP. It will be appreciated that in the tilt scanning mode, there is no linear movement of the ultrasound probe 502.

During operation in the tilt scanning mode, the ultrasound probe 502 scans the target region of interest as it moves along path TP and outputs ultrasound signals to the clinical ultrasound machine 500. The ultrasound signals from the ultrasound probe 502 are processed via the clinical ultrasound machine 500 to generate a plurality of 2D ultrasound images of the target region of interest at the desired frame rate (typically 15 or 30 frames per second). The 2D ultrasound images are communicated to the general purpose computing device 200 for processing. The general purpose computing device 200 in turn processes the 2D ultrasound images to reconstruct a 3D ultrasound image covering a pie-shaped volume of the scanned target region of interest according to a known method such as that described in above-incorporated U.S. Pat. No. 5,562,095 to Downey et al.

Turning to FIG. 7a, the start position of the actuator 250 in the compound scanning mode is shown. As can be seen, ultrasound probe 502 is positioned such that its longitudinal axis is approximately −30° to the normal of the surface of the target region of interest to be scanned. Each linear slide 308 is at its rearward most position on the respective stationary rail. As will be appreciated, each linear slide 308 is contained within casing 700, and thus is not visible in FIG. 7a.

FIG. 7b shows the finish position of the actuator 250 in the tilt scanning mode. As can be seen, ultrasound probe 502 is positioned such that its longitudinal axis is approximately 30° to the normal of the surface of the target region of interest to be scanned. Each linear slide 308 is also at its forward most position on the respective stationary rail. Again, as each linear slide 308 is contained within casing 700, it is not visible in FIG. 7b.

FIG. 7c shows both the start position and the finish position of the actuator 250 in the compound scanning mode. As can be seen, the ultrasound probe 502 moves from the start position to the finish position along a path indicated by arrow CP. As such, the ultrasound probe 502 performs a compound scan of the target region of interest when moved along path CP. Comparing the scan path of the ultrasound probe 502 during operation in the compound scanning mode (FIG. 7c) to the scan paths of the ultrasound probe 502 during operation in the linear scanning mode (FIG. 5c) and tilt scanning mode (FIG. 6c), a larger volume is covered by the ultrasound probe 502 during operation in the compound scanning mode.

During operation in the compound scanning mode, the ultrasound probe 502 scans the target region of interest as it moves along path CP. The ultrasound signals output by the ultrasound probe 502 are processed via the clinical ultrasound machine 500 to generate a plurality of 2D ultrasound images of the target region of interest at the desired frame rate (typically 15 or 30 frames per second). The 2D ultrasound images are communicated to the general purpose computing device 200 for processing. The general purpose computing device 200 in turn processes the 2D ultrasound images to reconstruct a 3D ultrasound image covering a frusto-conical shaped volume of the scanned target region of interest as will now be described below.

As will be appreciated, in the compound scanning mode, reconstructing a 3D ultrasound image from the plurality of 2D ultrasound images must take into account both the linear and tilt movements of the ultrasound probe 502. For this purpose, two 3D matrices are created within memory associated with the general purpose computing device 200 and mapped to one another.

The first 3D matrix, hereinafter referred to as an acquisition matrix, holds pixel values of each acquired 2D ultrasound image. The size of the acquisition matrix is expressed as:

$$h \times w \times n \quad (1)$$

where h is the number of pixels in each 2D ultrasound image along the Y-direction, w is the number of pixels in each 2D ultrasound image along the X-direction, and n is the number of 2D ultrasound images to be captured during the compound scan. It should be noted that the number of pixels in each 2D ultrasound image along the Y-direction h and X-direction w are fixed for the compound scan. The number of 2D ultrasound images to be captured n is determined by dividing the maximum sweeping angle of the ultrasound probe 502 by a desired angle between two consecutive 2D ultrasound images. The desired angle between two consecutive 2D ultrasound images is set by the user prior to ultrasound image acquisition via the user interface 600. As will be appreciated, the grey-value of each pixel may be one or two bytes depending on the number of bits selected to represent the grey-values. Prior to scanning, each pixel within the acquisition matrix is set to a value of zero, and thus is set to the color black.

The second 3D matrix, hereinafter referred to as a reconstruction matrix, holds grey-values of each voxel of the reconstructed 3D ultrasound image. The size of the reconstruction matrix is determined by the acquired image parameters, scanning mode, and maximum sweep either set as default values within the 3D ultrasound imaging system 100 or set by the user via the user interface 600. Specifically, the size of the reconstruction matrix is expressed as:

$$h \times w \times z \quad (2)$$

where h is the number of pixels in each 2D ultrasound image along the Y-direction and w is the number of pixels in each 2D ultrasound image along the X-direction. The value of z is calculated as:

$$z = (n-1)\left(1 + \frac{2h}{L}\sin(\theta)\right) \quad (3)$$

where n is the number of 2D ultrasound images to be captured, h is the number of pixels in each 2D ultrasound image along the Y-direction, L is the extent of the linear motion during the compound scan, and θ is the maximum angle of the tilt motion during the compound scan.

To determine an association between a voxel in the reconstruction matrix and a corresponding pixel in the acquisition matrix, a mapping matrix is used. In this embodiment, the mapping matrix is calculated using a closest point method, wherein a particular voxel within the reconstruction matrix is mapped to a pixel within the acquisition matrix that has coordinates closest thereto. The mapping matrix is calculated before the compound scan is performed and is used to fill each voxel within the reconstruction matrix as corresponding pixels within the acquisition matrix are filled based on the captured 2D ultrasound images. The mapping matrix is stored within memory associated with the general purpose computing device 200 and may be used with future compound scans comprising the same parameters (i.e. angular step angle, linear step distance, linear extent of scan L, maximum angle θ, size of image in X-direction, number of pixels in X-direction, and number of pixels in Y-direction). During the compound scan, the reconstruction matrix is displayed by the user interface 600 such that a user can follow the scanning and reconstructing process.

Figure 8:
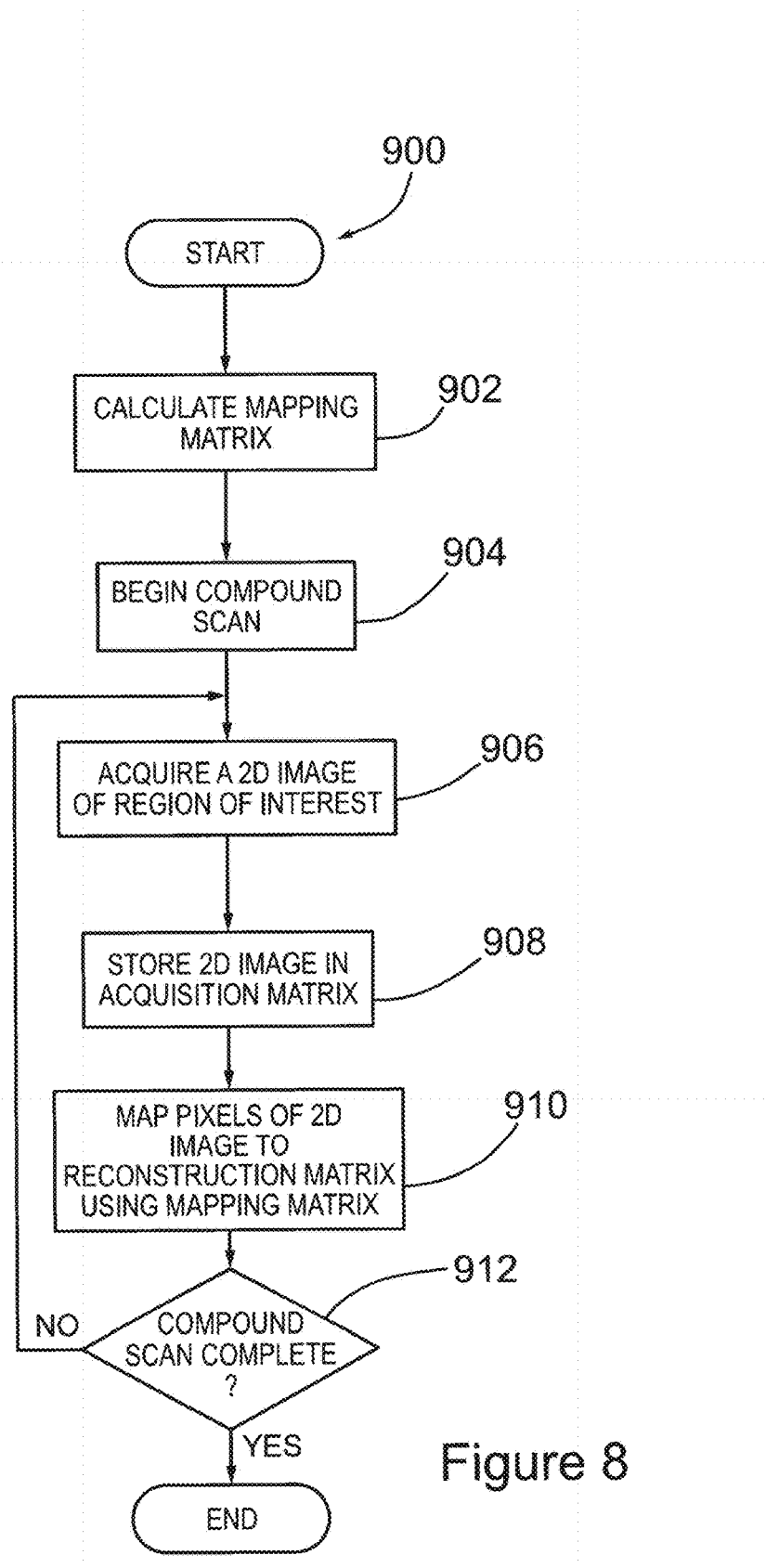
FIG. 8 is a flowchart showing a method for reconstructing a 3D ultrasound image during the compound scanning mode.

Turning to FIG. 8, a flowchart showing a method for reconstructing a 3D ultrasound image from a plurality of 2D ultrasound images obtained during a compound scan of the target region of interest is shown and is generally identified by reference numeral 900. Method 900 begins by calculating the mapping matrix (step 902). The mapping matrix is calculated by first transferring each pixel in the acquisition matrix according to corresponding 3D scanning geometry, and then using each transferred pixel to find a reverse map according to the closest point method. Each pixel ($X_{im(i)}$, $Y_{im(i)}$) in acquired 2D ultrasound image i in the acquisition matrix (containing a total number of acquired 2D ultrasound images n) is transferred to 3D geometry using the following equations:

$$X = X_{im(i)} \quad (4)$$

$$Y = Y_{im(i)} dx \cos(\theta_i) \quad (5)$$

$$Z = i \times dL + Y_{im(i)} dy \sin \theta_i \quad (6)$$

where the transformed 3D coordinates [X, Y, Z] represent the corresponding location in the 3D ultrasound image, $\theta_i$, is the angle of the ultrasound probe 502 at which 2D ultrasound image i is acquired, and dL is the linear scanning distance between two consecutive captured 2D ultrasound images. It is noted that the transformed 3D coordinates [X, Y, Z] do not necessarily contain integer values and do not directly correspond to a location within the reconstruction matrix, since coordinates within the reconstruction matrix are integer values. As will be appreciated, if only the integer part of the transformed 3D coordinates [X, Y, Z] is used, depending on the linear scanning distance between two consecutive captured 2D ultrasound images, there may be gaps between the planes in the reconstruction matrix that must be filled. Further, there may be cases wherein two or more pixels in the acquired 2D ultrasound images contain the same integer values.

Once the 3D transformation for each pixel ($X_{im(i)}$, $Y_{im(i)}$) in the acquisition matrix has been calculated according to Equations (4), (5) and (6), each voxel within the reconstruction matrix that falls within the boundaries of the scanned target region of interest is evaluated. In this embodiment, any voxel within the reconstruction matrix that is outside of the boundaries of the scanned target region of interest will have a grey-value that results in a black colored voxel. For each of these voxels, a pixel within the acquisition matrix that has coordinates closest to each particular pixel within the reconstruction matrix is identified, and the transformed 3D coordinates [X, Y, Z] of that pixel are recorded within the mapping matrix.

To minimize processing, given the geometry of the scanned volumes, once a single slice perpendicular to the compound scan direction within the mapping matrix is calculated, the remaining slices within the mapping matrix are determined by changing the value of X. To further minimize processing, given the symmetry about the mid-line of the compound scan, that is, when the ultrasound probe 502 is positioned such that its longitudinal axis is generally perpendicular to the surface of the target region of interest to be scanned, once half of the pixels in a slice have be calculated for the mapping matrix, the second half of the pixels can be readily determined by mirroring the Y value of the calculated pixels. As will be appreciated, each element within the mapping matrix has three components represented by $X_{im(i)}$, $Y_{im(i)}$ and the acquired 2D ultrasound image number i.

Once the mapping matrix has been calculated, the compound scan begins (step 904). A 2D ultrasound image of the target region of interest is acquired (step 906) and stored in the acquisition matrix (step 908). The pixels of the acquired 2D ultrasound image are mapped to corresponding voxels within the reconstruction matrix using the mapping matrix, and the resulting reconstruction matrix is displayed on the user interface 600 (step 910). A check is performed to determine if the compound scan is complete (step 912). If the compound scan is not complete, the method returns to step 906 to acquire another 2D ultrasound image of the region of interest. Once all of the 2D ultrasound images of the compound scan have been acquired and processed as described above, the method ends.

Figure 9:
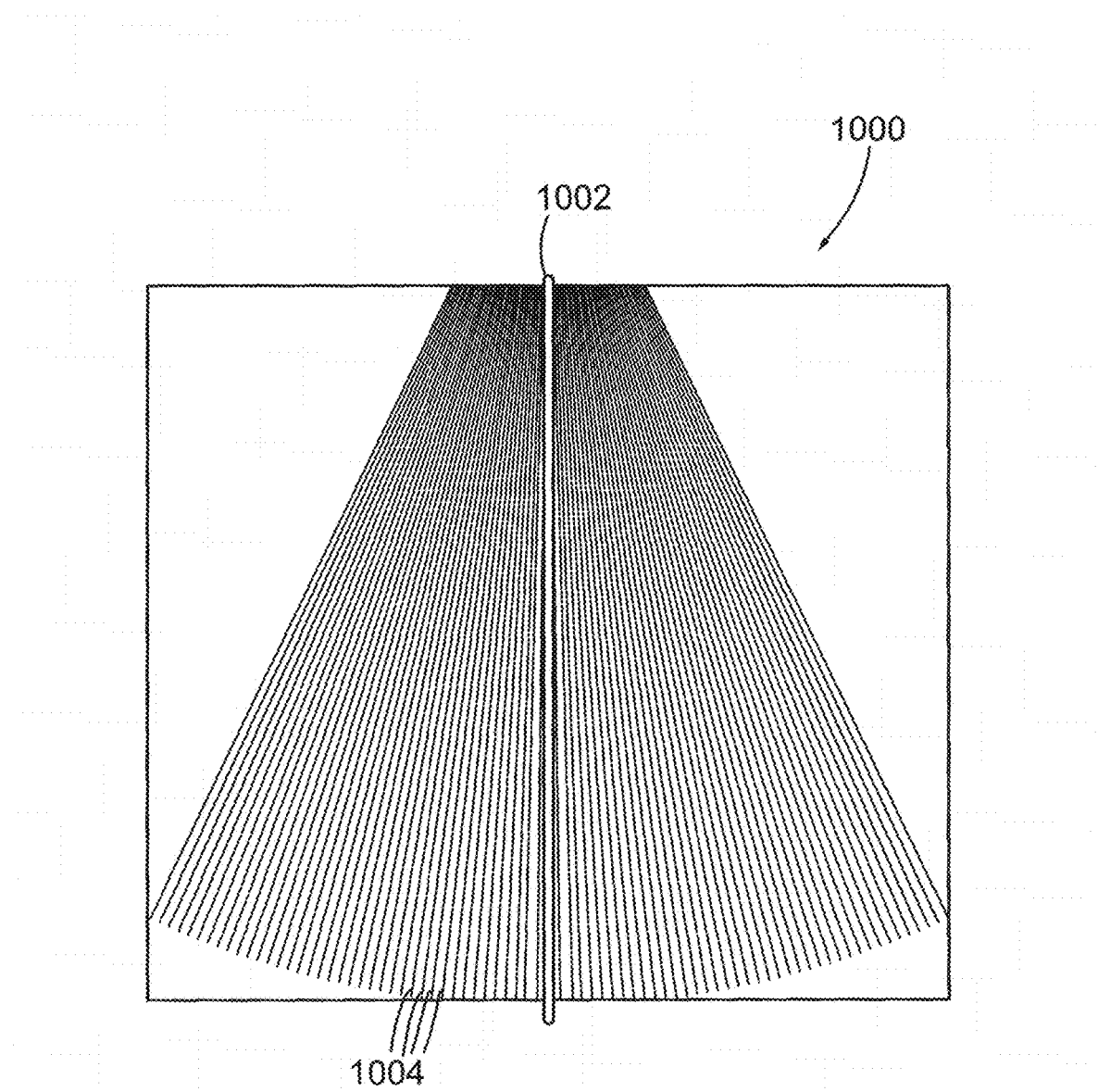
FIG. 9 is an exemplary ultrasound image reconstructed according to the method of FIG. 8.

A side view of an exemplary ultrasound image 1000 reconstructed according to method 900 is shown in FIG. 9. Reconstructed image 1000 was acquired using a linear scanning distance L of 25 cm and a maximum angle θ of 27°. As can be seen, reconstructed image 1000 is symmetric about center line 1002, which is shown for illustrative purposes. Each line 1004 represents the side view of a single 2D ultrasound image stored within the reconstruction matrix.

Although the mapping matrix is calculated above using a closest point method, in another embodiment the mapping matrix may be calculated using an interpolation method, wherein the grey-value of a particular voxel within the reconstruction matrix is determined using the grey-value of a combination of pixels within the acquisition matrix that have coordinates closest to the particular voxel within the reconstruction matrix. In this embodiment, once the 3D transformation for each pixel ($X_{im(i)}$, $Y_{im(i)}$) in the acquisition matrix has been calculated according to Equations (4), (5) and (6), a linear combination of 2, 4 or 6 pixels within the acquisition matrix that have coordinates closest to each particular voxel within the reconstruction matrix are identified, the grey-value of each of these pixels is used to calculate the grey-value of the corresponding voxel in the reconstruction matrix, and the transformed 3D coordinates [X, Y, Z] of each of the 2, 4 or 6 pixels are stored in the mapping matrix. As will be appreciated, if 2 pixels are used, each pixel within the mapping matrix will contain 8 components represented by $X_{im(i)}$, $Y_{im(i)}$ and the acquired 2D ultrasound image number i for each of the 2 pixels identified in the acquisition matrix, as well as 2 values associated with the weighting factors of the 2 pixels. If 4 pixels are used, each pixel within the mapping matrix will contain 16 components represented by $X_{im(i)}$, $Y_{im(i)}$ and the acquired 2D ultrasound image number i for each of the 4 pixels identified in the acquisition matrix, as well as 4 values associated with the weighting factors of the 4 pixels. Similarly, if 6 pixels are used, each pixel within the mapping matrix will contain 24 components represented by $X_{im(i)}$, $Y_{im(i)}$ and the acquired 2D ultrasound image number i for each of the 6 pixels identified in the acquisition matrix, as well as 6 values associated with the weighting factors of the 6 pixels.

Those skilled in the art will appreciate that virtually any type of ultrasound probe may be used and virtually any type of clinical ultrasound machine that is compatible with the selected ultrasound probe may be used. For example, clinical ultrasound machines utilizing B-mode ultrasound, Doppler imaging ultrasound, or power Doppler imaging ultrasound may be used.

Although the linkage arms are described above as being made of aluminum, those skilled in the art will appreciate that other types of material may be used such as for example stainless steel, plastic materials, etc.

Although the linear motor system is described above as comprising a linear slide to provide movement along a single axis, those skilled in the art will appreciate that other arrangements may be used. For example, a box slide or dovetail may be used. Similarly, the linear movement may be achieved through use of rods or round rails. Also, although the linear motor system is described above as comprising a motor driven lead screw to provide movement along a single axis, those skilled in the art will appreciate that other arrangements may be used. For example, devices such as a belt, chain, rack and pinion gearing may be used.

Although the tilt motor system is described above as comprising a motor directly connected to one or more linkage arms, the tilt motor system may alternatively use one or more gears to adjust the speed of the tit motor system.

Although the linear motor system and tilt motor system are described above as comprising separate motors, those skilled in the art will appreciate that one motor may be used. For example, a single motor may be used in combination with a specific orientation of linkage arms to operate within tilt and linear motion parameters, thereby achieving proper motion for a compound scan. It will also be appreciated that different types of motors may be used such as for example brushed DC motors.

Although the ultrasound probe is described above as being retained within the housing assembly via a harness, those skilled in the art will appreciate that other types of mechanical retaining devices may be used. For example, a quick release mechanism or spring-loaded quick release mechanism may be used to retain the ultrasound probe within the housing assembly.

Although voxels within the reconstruction matrix are considered to be outside of the scanned target region of interest if they are black in color, those skilled in the art will appreciate that the voxels to be evaluated may be selectable by a user via user interface 600.

In embodiments described above, particular motor gear ratios and output speeds, lead screw pitches, path distances, sweeps and speeds as well as particular component materials have been specified. Those of skill in the art will appreciate that these specifics are exemplary and that alternatives are available.

Although embodiments have been described with reference to the drawings, those of skill in the art will appreciate that variations and modifications may be made without departing from the scope thereof as defined by the appended claims.

What is claimed is:

1. An ultrasound probe actuator comprising:
   a housing assembly configured to accommodate an ultrasound probe and to be positioned adjacent to a target region of interest to be examined;
   motors coupled to the housing assembly, the motors configured to move the housing assembly in a manner to allow the ultrasound probe when accommodated by the housing assembly to perform a compound scan of the target region of interest;
   a casing enclosing at least the motors; and
   user actuatable controls in the form of operational buttons on the casing to start/stop the compound scan.

2. The actuator of claim 1 wherein during the compound scan, the motors are configured to move the housing assembly along a linear path and to tilt the housing assembly during its movement along the linear path.

3. The actuator of claim 2 wherein the motors comprise a first motor and a second motor, the first motor being configured to move the housing assembly along the linear path and the second motor being configured to tilt the housing assembly.

4. The actuator of claim 3 wherein the first motor is coupled to a linear slide carriage for moving the housing assembly along the linear path.

5. The actuator of claim 4 wherein the linear slide carriage is coupled to a pair of linear slides and wherein an interior surface of the casing has a pair of stationary rails formed thereon, said stationary rails being configured to support the linear slides.

6. The actuator of claim 5 wherein the casing further encloses a portion of the housing assembly.

7. The actuator of claim 6 wherein the casing has grooves formed therein shaped to accommodate a user's fingers and wherein the user actuatable controls are positioned within the grooves.

8. The actuator of claim 3 wherein the second motor is coupled to a plurality of linkage arms for tilting the housing assembly between first and second boundaries.

9. The actuator of claim 8 wherein the first and second boundaries are defined by first and second angles measured with respect to the normal to a surface of the target region of interest.

10. The actuator of claim 9 wherein the first and second angles are complimentary.

11. The actuator of claim 9 wherein the first angle is equal to approximately 30° and the second angle is equal to approximately −30°.

12. The actuator of claim 2 wherein the motors are further configured to move the housing assembly along the linear path to allow the ultrasound probe when accommodated by the housing assembly to perform a linear scan of the target region of interest or to tilt the housing assembly to allow the ultrasound probe when accommodated by the housing assembly to perform a tilt scan of the target region of interest.

13. The actuator of claim 1 wherein the housing assembly comprises a harness to retain the ultrasound probe therein.

14. The actuator of claim 1 wherein the casing has grooves formed therein shaped to accommodate a user's fingers and wherein the user actuatable controls are positioned within the grooves.

15. The actuator of claim 14 wherein the casing is formed of molded plastic material.

16. An ultrasound imaging system comprising:
    the ultrasound probe actuator according to claim 1;
    the ultrasound probe accommodated by the housing assembly of the actuator; and processing structure configured to process ultrasound signals output by the ultrasound probe and to control the motors of the actuator.

17. The ultrasound imaging system of claim 6 wherein the processing structure comprises a clinical ultrasound machine to which the ultrasound probe is connected, the clinical ultrasound machine being configured to generate a succession of two-dimensional ultrasound images during the compound scan, and a processing device configured to reconstruct the two-dimensional ultrasound images to form a three-dimensional ultrasound image of the target region of interest.

18. The actuator of claim 1 wherein the casing further encloses a portion of the housing assembly.

19. The actuator of claim 18 wherein the casing has grooves formed therein shaped to accommodate a user's fingers and wherein the user actuatable controls are positioned within the grooves.

20. The actuator of claim 19 wherein the casing is formed of molded plastic material.

* * * * *